United States Patent [19]

Steinman

[11] Patent Number: 5,516,292
[45] Date of Patent: May 14, 1996

[54] PRIMER DIRECTED NUCLEIC ACID AMPLIFICATION INCLUDING THE ADDITION OF SPECIFIC TEMPLATE DNA INACTIVATING ENZYME

[75] Inventor: Charles R. Steinman, New York, N.Y.

[73] Assignee: The Research Foundation of State University of New York, Albany, N.Y.

[21] Appl. No.: 694,902

[22] Filed: May 2, 1991

[51] Int. Cl.⁶ .............................. C12P 19/34; C12Q 1/68
[52] U.S. Cl. ................................. 435/91.2; 435/6
[58] Field of Search .................... 435/6, 91, 172.3, 435/91.2; 536/27, 23.1

[56] References Cited

U.S. PATENT DOCUMENTS 4,800,159   1/1989   Mullins et al. .................. 435/172.3
5,427,929   6/1995   Richards et al. ................. 435/91.2

OTHER PUBLICATIONS

Strom et al. (1989), Am. J. Hum. Genet. 45 (Suppl. 4), A221.
Furrer et al. (Jul. 1990), Nature 346, 324.
Sambrook et al. (1989), Molecular Cloning: A Laboratory Manual, 2nd Ed. (Cold Spring Harbor Press), pp. 14.2, 14.15, 5.3–5.9.

*Primary Examiner*—Mindy Fleisher
*Assistant Examiner*—Philip W. Carter
*Attorney, Agent, or Firm*—Hoffmann & Baron

[57] ABSTRACT

Methods for the enzymatic reduction and/or elimination of contaminant DNA from enzymatic amplification procedures are disclosed. These methods include the use of restriction endonucleases, DNAases and exonucleases which act upon contaminant DNA in polymerase chain reaction mixtures such that contaminant DNA is not amplified.

6 Claims, 4 Drawing Sheets

FIG. 1

2 Complementary DNA Strands
$\overline{A}$ = Site Complementary to Primer A
$\overline{B}$ = Site Complementary to Primer B
A, B = Oligonucleotide Primers Double Stranded DNA Template Which is to be Multiplied ↓ Denature, Reanneal ↓ Taq DNA Polymerase (Extends DNA in 5' to 3' Direction)

dNTPs (Deoxyribonucleoside Triphosphates)

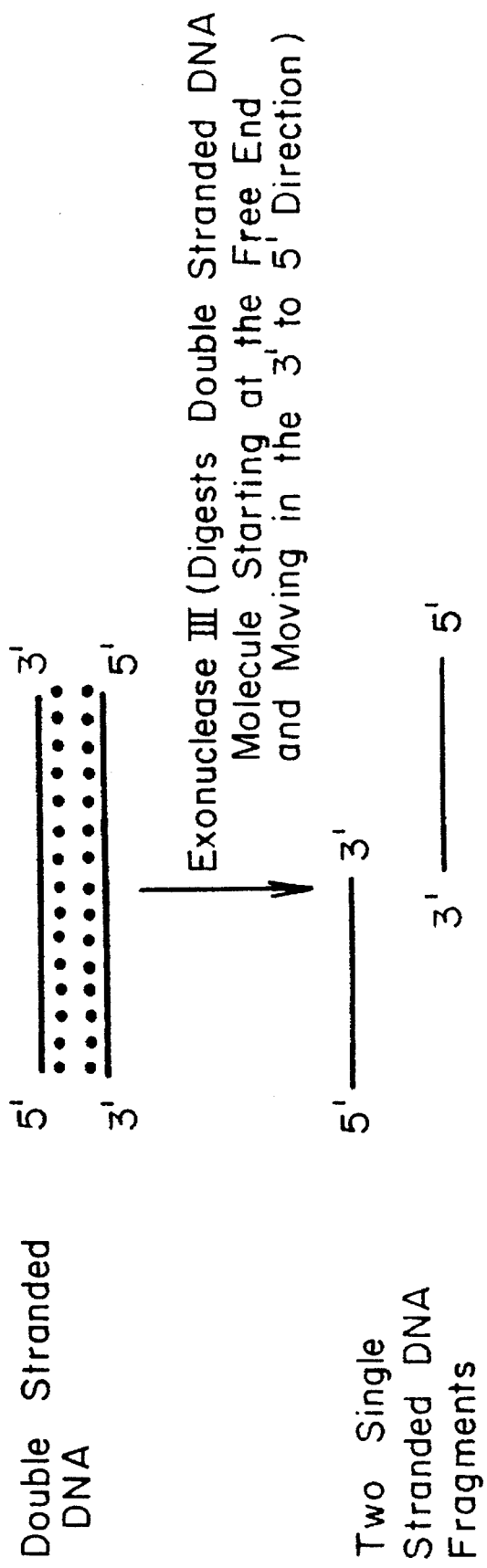
FIG. 2(a) THE USE OF EXONUCLEASE III

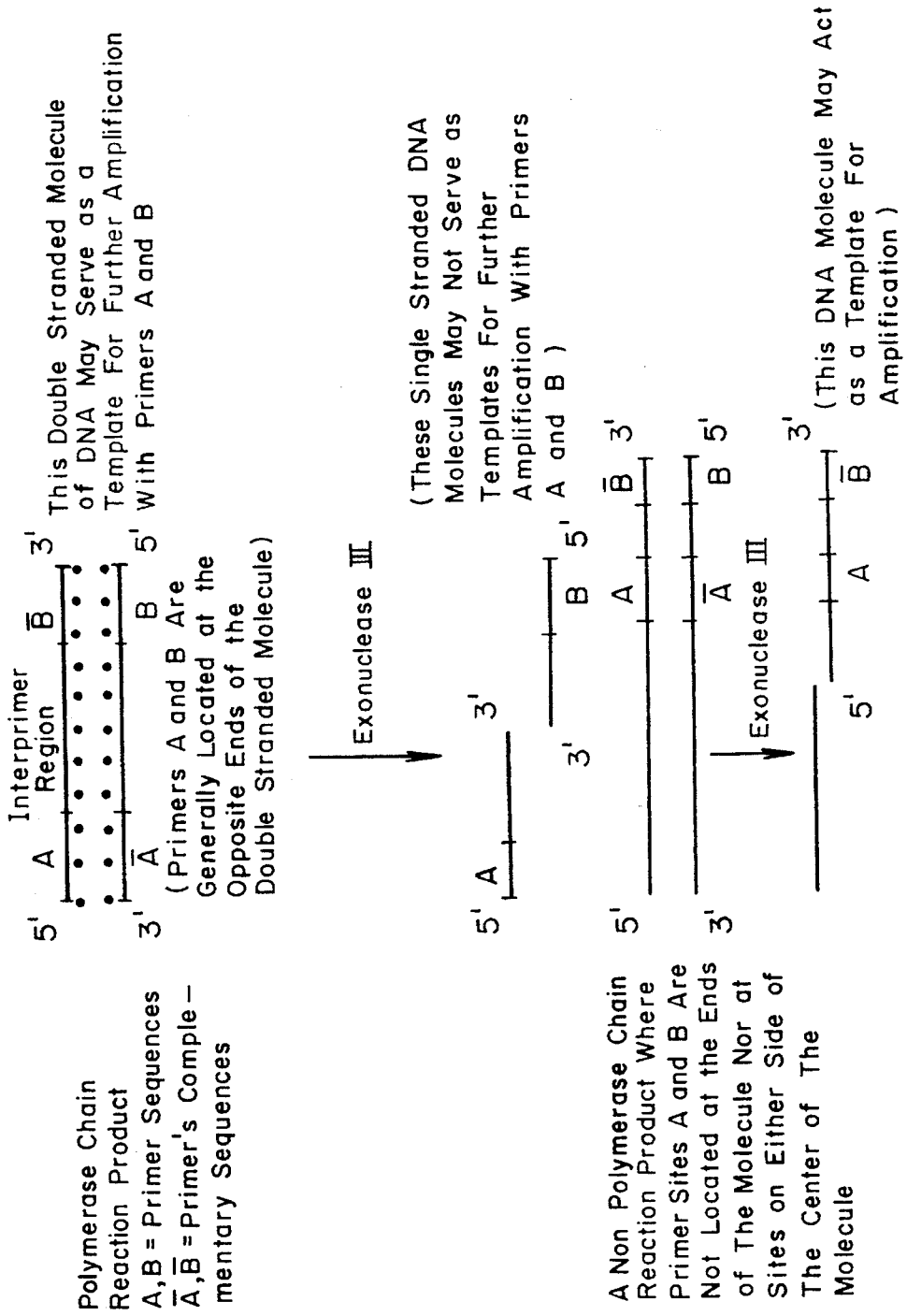

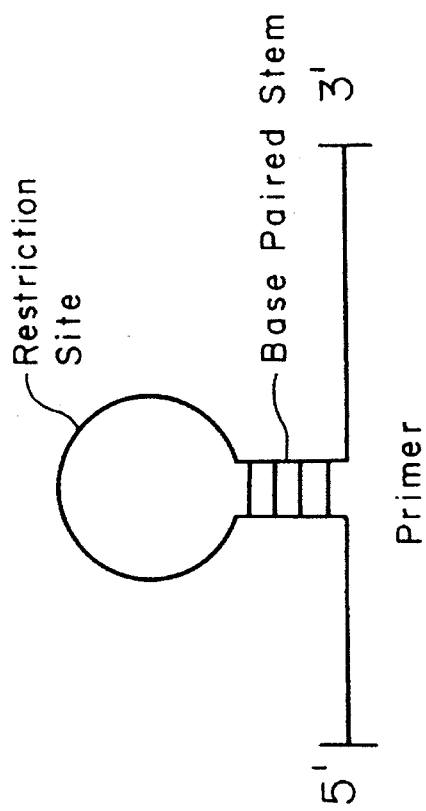
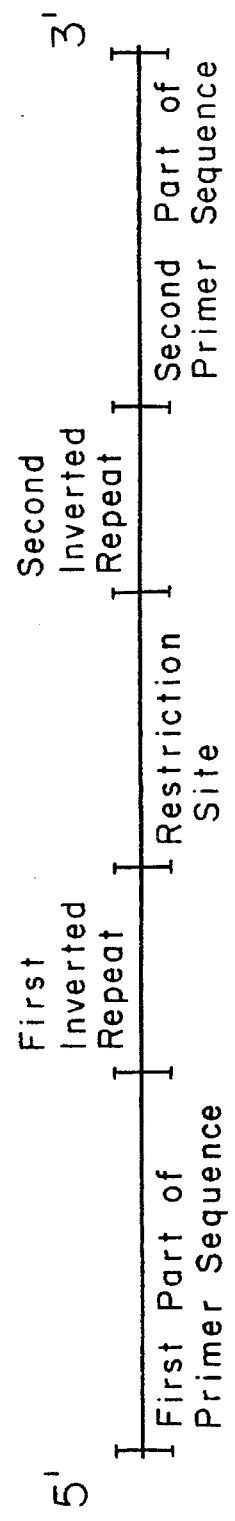
FIG. 3A
FIG. 3B — Loop and Primer Sequence of FIG. 3A Drawn Linearly

PRIMER DIRECTED NUCLEIC ACID AMPLIFICATION INCLUDING THE ADDITION OF SPECIFIC TEMPLATE DNA INACTIVATING ENZYME

BACKGROUND OF THE INVENTION

The present invention relates to the art of enzyme amplification, and, in particular, it concerns the use of the polymerase chain reaction for the enzymatic amplification of nucleic acids.

Several methods are known for the synthesis of nucleic acids from an existing sequence. These methods are capable of producing large amounts of a given nucleic acid of a specified sequence. U.S. Pat. No. 4,683,202 to Mullis and U.S. Pat. No. 4,800,159 to Mullis, et al., which are incorporated herein by reference, disclose the GENEAMP™ polymerase chain reaction method by which a length of target DNA (template) is replicated in an amplification process involving the use of Taq DNA polymerase as illustrated in FIG. 1. The DNA template is defined by two sites of a specific base sequence to which two oligonucleotide primer DNA molecules have been synthesized. Each primer is complementary to a base sequence at either end of the target DNA sequence and anneals to it such that extension by Taq DNA polymerase occurs in a direction toward the site of the other primer.

U.S. Pat. No. 4,800,159 to Mullis, et al. discloses the incorporation of restriction sites onto or into the 5' ends of primers used in an amplification process to produce amplified DNA with restriction sites at its ends. When cut with the appropriate enzymes, the amplified product can be inserted into plasmid or viral vectors and cloned. Mullis et al. further disclose the treatment of a nucleic acid with a restriction endonuclease prior to amplification. A cut sequence would not be amplified and the appearance of an amplified sequence would indicate that the amplified sequence does not have a restriction site specific for the restriction endonuclease. Mullis, et al. do not teach the incorporation of a restriction enzyme recognition site into a primer for the purpose of eliminating a contaminant PCR product from a subsequent PCR amplification process. Furthermore, Mullis, et al. do not disclose the treatment of contaminant PCR product with a restriction endonuclease to cleave the interprimer region such that the contaminant PCR product cannot be amplified in a subsequent PCR process.

It is possible to make many copies of the target DNA, by placing template DNA, Taq DNA polymerase, deoxyribonucleotide triphosphate precursors and other components into a reaction mixture and treating the reaction mixture with a sequence of heating steps. Typically, this involves an annealing phase at 45°–55° C., an extension phase at 70°–75° C., and a denaturation phase at 94° C. During each cycle, (which includes each of the steps) the amount of target template DNA is increased theoretically by two-fold and over a million fold after twenty cycles.

The great sensitivity of the GENEAMP™ polymerase chain reaction method for the amplification of DNA requires that the amount of contaminant template DNA (DNA whose multiplication is not desired) be kept to a minimal level or be altered in such a way that it cannot undergo the multiplication process. The polymerase chain reaction method is so sensitive that only a small sample of template DNA is needed for multiplication to occur. Therefore, the presence of even a minute quantity of contaminant template DNA containing the target sequence could quite possibly result in the amplification of the contaminant template DNA and a mixture of amplified template and amplified contaminant template DNA. It is noted that the methods of the present invention are suitable for other methods of primer-dependent amplification of DNA and that the GENEAMP™ polymerase chain reaction method is used for exemplary purposes.

Two kinds of contamination with template DNA are most prevalent. The first type of contamination results from the presence of the product of a previous amplification in which the same target sequence was amplified with the same primers. Such DNA, can itself serve as template DNA. The second type of contamination results from the presence of template DNA which was not produced in a previous polymerase chain reaction process. This may occur for example, when a small amount of a DNA target-containing solution (e.g., from a genomic DNA extract) contaminates a solution which does not contain a target.

The first type of contamination is more difficult to eliminate. This is because polymerase chain reaction products are often present in very high copy number in completed amplification reactions (as high as $10^{12}$ copies). Since the polymerase chain reaction process has a potential of detecting and multiplying even a single molecule (or copy), the presence of even an exceedingly small amount of contaminant target DNA may result in significant contamination.

Therefore, even the use of such routine procedures as pipetting or the opening and closing of the reaction mixture container may result in the introduction of a sufficient amount of aerosolized material to interfere with the diagnostic use of the polymerase chain reaction method. Routine containment methods often fail to prevent the accumulation over time of such contaminant target DNA molecules in the local environment. Even the segregation of the amplified products in a separate laboratory has not generally succeeded in removing contaminant template DNA. This problem is particularly acute in those situations where the same set of primers are used repeatedly on the same target sequence, as is often the case in such amplifications. Efforts have been made to eliminate the contamination problem. These efforts have resulted in only limited success in reducing contamination.

It is therefore an object of the invention to significantly reduce and/or eliminate from amplification reactions the presence of amplifiable contaminant target DNA arising from previous similar amplification reactions (i.e., reactions using the similar primers and similar target sequences).

It is a further object of the present invention to enzymatically act upon contaminant DNA or contaminant target DNA arising from previous similar amplification reactions (i.e., reactions using the same primers and the same target sequence) or to otherwise alter or eliminate such contaminant DNA such that the contaminant DNA is no longer capable of being amplified.

It is yet another object of the present invention to heat-inactivate enzymes used to inactivate contaminant DNA in such a manner that the reaction mixture need not be exposed to the atmosphere and possible recontamination until completion of the amplification process.

SUMMARY OF THE INVENTION

These and other objects are achieved by the present invention which provides enzymatic methods for the inactivation of contaminant target DNA in a DNA amplification process.

A preferred embodiment of an improved method for the amplification of DNA template involves the addition of a double strand specific 3' to 5' digesting agent, such as exonuclease III, to an amplification reaction mixture solution containing contaminant double stranded DNA. The solution is incubated for a time sufficient, and at a temperature sufficient for the digesting agent to digest double-stranded DNA in such a way as to render contaminating target DNA (i.e., a previously synthesized PCR product) non-amplifiable while leaving non-contaminating PCR product template DNA amplifiable.

An important advantage of this embodiment is that it allows the contaminant template DNA to be inactivated while leaving non-contaminant template DNA amplifiable. It achieves this by taking advantage of the fact that contaminant template DNA carries its primer sites at or near the ends of the molecule whereas virtually all other template DNA molecules not arising themselves from a previous PCR reaction, do not have their primer sites so located and in general have their primer sites located with random relationships to the ends of the individual DNA molecules.

An alternative embodiment involves the addition of DNAase I to an amplification reaction mixture solution containing contaminant DNA and Taq DNA polymerase. The solution is incubated for a time sufficient, and at a temperature sufficient, to inactivate the contaminant DNA. The DNAase is then inactivated by heating the solution at a temperature of about 90° C. for about 30 minutes. Unlike the previous method, this would fail to distinguish between contaminating and non-contaminating target DNAs.

In another alternative embodiment, at least one restriction endonuclease is added to an amplification reaction mixture solution containing contaminant double stranded DNA. The restriction endonuclease is specific for at least one restriction endonuclease recognition site in the primer or interprimer region, of the contaminant DNA, with a cutting site located such as to result in the production of a non-amplifiable cleavage product. The solution is incubated at a temperature sufficient, and for a time sufficient, for cleavage of the contaminant DNA template.

The polymerase chain reaction method has many applications and is of great importance to the detection and/or identification of microbial DNA in clinical specimens. It is also of great use in the characterization of biological forensic specimens and the identification of the source of the specimens. The polymerase chain reaction method is also useful for the pre-natal diagnosis of certain genetic disorders and the determination of the sex of a fetus. Further, the polymerase chain reaction method is useful in the diagnosing of the presence of specific nucleic acid sequences, such as those found in certain genetic disorders, and diagnostic kits applicable thereto. Amplification is most useful when the amount of target nucleic acid available for analysis is very small.

Accordingly, the present invention permits the removal of contaminant DNA from samples which otherwise would not be suitable for use in a polymerase chain reaction method. Furthermore, the present invention enhances the wide scale usage of the polymerase chain reaction method by eliminating contaminant DNA.

Another advantage is that certain embodiments of the present invention permit the specific elimination of contaminating DNA derived from previous PCR reactions while leaving intact other DNA molecules necessary to the amplification reaction (i.e., the target DNA template and oligonucleotide primers). Moreover, in the case of enzymatic digestion of contaminating DNA template, the process can be arrested by heat-inactivation of the enzyme without affecting the heat stable Taq polymerase. This allows the decontaminated reaction mixture not to be exposed to the atmosphere and possible recontamination until completion of the amplification process.

Yet another advantage of the present invention is that it permits the automation of the methods for the inactivation of contaminant DNA along with the polymerase chain reaction method, by use of a programmable cycling device.

The aforementioned methods may be combined where appropriate. For example, exonuclease III and one or more restriction endonucleases may be incorporated into a reaction mixture for the more effective digestion of contaminant DNA.

For a better understanding of the present invention, reference is made to the following description, taken in conjunction with the following figures, the scope of which is pointed out in the claims.

BRIEF DESCRIPTION OF THE DRAWINGS

FIG. 1 illustrates the method for the amplification of DNA by the GENEAMP™ polymerase chain reaction.

FIG. 2(a) illustrates the cleaving of DNA by exonuclease III; and

FIG. 2(b) illustrates the action of exonuclease III upon a GENEAMP™ polymerase chain reaction product and a target not derived from a PCR product.

FIG. 3(a) illustrates a primer having a base paired stem, a loop and a restriction site within the loop; and FIG. 3(b) illustrates the primer of FIG. 3(a) drawn linearly.

DETAILED DESCRIPTION OF THE INVENTION

The term "primer" as used herein (with respect to the GENEAMP™ polymerase chain reaction) refers to an oligonucleotide (a short nucleic acid chain), which is capable of acting as a point of initiation of synthesis when placed under conditions in which synthesis of a primer extension product, which is complementary to a nucleic acid strand, is induced. The primer may occur naturally, as in a purified restriction digest or be produced synthetically.

The term "interprimer region" as used herein refers to the sequence of target DNA or PCR product DNA which is present in the region between the primers and their complements.

The term "contaminant PCR product" as used herein refers to the DNA produced from a previous similar PCR reaction (i.e. a PCR employing similar primers and target sequences). The double stranded PCR product carries a primer on each strand. The primers are located at opposing ends of the strands. Each strand of DNA includes a sequence complementary to the primer in the other strand.

By convention, single stranded DNA chains are read 5' to 3' in a left to right direction. In double stranded DNA the complementary chains run antiparallel to each other. A 5' direction in one strand implies a 3' direction in the complement of that strand and vice versa.

I. THE USE OF EXONUCLEASE III (EXO III) OR SIMILAR ENZYMES

The present invention includes the use of heat-labile reagents, such as enzymes, to inactivate contaminant DNA and prevent the amplification of contaminant DNA in the PCR. A preferred embodiment includes the use of an exonuclease which only acts upon double stranded DNA molecules (i.e. those DNA molecules in which each base is hydrogen-bonded to a complementary base on the opposite strand of DNA), and which begins digestion of the double stranded DNA at either the 3' end or the 5' end. Suitable enzymes include, for example, exonuclease III (which digests double stranded DNA in a 3' to 5' direction) and T7 exonuclease (gene 6). T7 exonuclease (gene 6) digests double stranded DNA in a 5' to 3' direction. The digestion of double stranded DNA by exonuclease III is illustrated in FIGS. 2(a) and 2(b).

The two antiparallel strands of DNA are digested at about the same rate and in opposite directions. Digestion ceases when all the double stranded DNA is exhausted and only single stranded DNA remains. This usually occurs when each strand of double stranded DNA has been digested about to its midpoint.

A number of other enzymes have similar double-strand-specific exonuclease activity. In some cases, double-strand-specific exonuclease activity is coupled with other enzymatic activities, for example, T4 DNA polymerase has double-strand-specific exonuclease and polymerase activity. In some instances these other activities can be differentially inhibited. For example, the polymerase activity of T4 DNA polymerase can be inhibited by omitting the deoxyribonucleotide triphosphate precursors.

To be an effective template for the PCR process, a single stranded DNA molecule must possess two specific DNA sequences, one at each end of the sequence to be amplified. At the 3' end there must be a sequence substantially complementary to an oligodeoxynucleotide primer. The primer need not be exactly complementary to the target template nucleotide sequence. The primer need only be complementary to the target DNA such that after base pairing to the 3' end of the target sequence, the primer can be extended by a polymerase enzyme so as to form a new chain of DNA with a sequence substantially complementary to the original strand and extending at least to the 5' end of the original strand.

At the 5' end of the template there must be a sequence substantially complementary to the complement of a second oligonucleotide primer (i.e., substantially the same as the second oligonucleotide primer). The second primer can then initiate a similar cycle of synthesis which starts with the hydrogen bonding of the second primer to its complementary sequence at the 3' end of the newly synthesized strand. Thus, the original target strand of DNA must have at one end a sequence that is substantially the same as one primer and, at the other end, one that is substantially complementary to the other primer.

An essential point is that a specific sequence of DNA must be present at each end of a proposed target sequence of DNA in order for it to be amplified by the PCR. Because of this requirement, the single stranded DNA which results from the digestion of a double stranded contaminant PCR product by exonuclease III (or a similar enzyme) cannot serve as a template for further amplification by those same primers since the digested contaminant PCR product DNA will each carry only one, but not both, of these necessary sequences at its ends. This results from the fact that in PCR products the primers are at or near the ends of the double stranded DNA molecule.

Most naturally occurring (or even cloned) target DNA templates would not have primer sites located at the ends or even at either side of the center of a DNA molecule. Thus, it is unlikely that target DNA would be inactivated. This is due to several factors. First, the probability that a target sequence only a few hundred bases long would be located just at the center of a piece of DNA (that is typically several thousand or more bases long) is small.

Moreover, in most instances the DNA molecules from which the target is to be amplified will be derived from much longer molecules which are frequently many millions of bases long as occurs in genomic DNA. Accordingly, the actual DNA molecules examined are broken during extraction and handling into shorter lengths. This breakage is essentially random so that even if a few such molecules happened to break such that the target sequence happened to straddle the midpoint, the vast majority of molecules, would not and the vast majority of the DNA therefore would not be inactivated by the enzymatic digestion described. In general, half of the DNA from such molecules (DNA having a target sequence which does not straddle the midpoint) would be digested, leaving half as much target DNA as before. For a process such as the PCR which amplifies many thousands or millions of times, the loss of half the target would not be expected to decrease the sensitivity of the final reaction in an important way.

Double strand specific exonucleases (and similar enzymes) will generally inactivate any potential target DNA template which has primer sites located on either side of the midpoint of a double stranded DNA molecule. In practice the exonucleases do not digest precisely to the center of linear double stranded DNA molecules (i.e., there is some variation in the rate of digestion from each end so that the single stranded products are terminated near, but not necessarily exactly, at the middle). In amplifiable contaminant PCR product contaminants, the sites to be digested are not near the middle but are at or near the ends.

Certain PCR product molecules might end unevenly and have overhanging ends. This can be caused by a variety of factors. Unless the overhanging ends are more than one or two bases long (which is unlikely) and occur at the 3' end in the case of a 3' to 5' exonuclease (such as Exo III) or the 5' end in the case of a 5' to 3' exonuclease (such as T7 exonuclease) the overhang would inhibit the action of the exonuclease only slightly and therefore not interfere in a practical way with this method.

These double-strand-specific exonucleases would not affect the single stranded DNA primers unless the 3' termini of the primer formed base pairs to a significant extent. This would not normally be the case. However, if the primers did for some reason form such double stranded molecules, they could possibly be inactivated by the exonuclease and would have to be excluded from the enzymatic digestion reaction. In other words, the primers would be added to the reaction mixture after the digestion was complete and the exonuclease had been inactivated.

Thus, in the vast majority of situations contaminant PCR product and the non-PCR product templates and primers will have different susceptibilities to exonuclease III (or a similar enzyme) digestion. This permits the exonuclease III (or a similar enzyme) to act specifically upon contaminant PCR product such that it is no longer an effective template for PCR amplification and is removed as a contaminant, without affecting other essential reactants.

Thus, the differential susceptibility of contaminant PCR product and non-PCR product templates permits one to distinguish between reactions which are detecting contaminant PCR product and reactions which are detecting non- PCR product templates since the contaminant PCR product, but not the non-PCR product templates, would be decreased or eliminated by exonuclease III (or a similar enzyme) digestion. Moreover, exonuclease III (or a similar enzyme) digestion could be employed to minimize or eliminate reaction products that result from amplification of templates consisting of contaminant PCR product molecules relative to the products of amplification resulting from amplification of targets derived from non-PCR target template.

Since the essential reactants including the single stranded DNA primers are not susceptible to digestion by exonuclease III (or a similar enzyme). This method affords the additional advantage of allowing a complete PCR reaction mixture to be acted upon by exonuclease III (or a similar enzyme) since the essential DNA components (template and primers) would be resistant to digestion and only the contaminating PCR product DNA, if any, would be digested.

If the exonuclease III digested reaction mixture is heated to 90° C. for 5 minutes (or at some other suitable temperature and time) the exonuclease III is completely inactivated but the remainder of the reaction mixture is still intact including the heat-resistant Taq polymerase (or other similar enzyme). Most other enzymes possessing similar exonuclease activity would also be inactivated by this heat treatment. These enzymes include, for example, T4 DNA polymerase and T7 exonuclease. Since the exonuclease is inactivated, it cannot act upon newly amplified PCR products produced within the reaction mixture.

Therefore, an important advantage of this method is that the reaction tubes do not have to be opened between the time in which contaminating PCR product is inactivated and the time in which amplification of the target is completed. Thus, recontamination of the reaction mixture is prevented. Accordingly, the process can be automated by adding exonuclease III (or a similar enzyme) to a complete PCR reaction mixture, sealing the tubes, permitting the exonuclease III (or a similar enzyme) to digest the contaminant PCR product and then heat inactivating the exonuclease III (or a similar enzyme). The PCR temperature cycling reaction could then be carried out. All of these steps can be automated by use of a programmable temperature cycler.

In theory, the 3' to 5' digestion of exonuclease III might be expected to be partially counteracted by the 5'-to-3' synthetic activity of a DNA polymerase, (such as Taq polymerase). Thus, the Exo III might be slightly less effective than an exonuclease which works in the opposite direction (such as T7 exonuclease). However, this is not a significant problem since an excess of exonuclease III will overcome the 5' to 3' synthetic activity of a DNA polymerase. The possibility of resynthesis from incompletely digested (and thus still base paired) or asymmetrically digested strands (by mosaic formation) might also be a theoretical shortcoming but this has not been an important obstacle and in any case would not be a problem with T7 exonuclease since it digests in the opposite direction (i.e., 5' to 3').

It is important to note that both exonuclease III and T7 exonuclease are active either in the standard PCR reaction mixture (containing 1.5 to 5 mM magnesium chloride) or in a slightly modified one (e.g. with 1 mM dithiothreitol added to it, as may help stabilize T7 exonuclease). This and similar modifications do not significantly impair the amplification reaction.

If a set of primers were inactivated by exonuclease (or a similar enzyme) digestion (for example, if the primers formed base pairs at one end) a similar enzyme digesting in the opposite direction would probably work since it would be very unlikely that both ends of the primers would base pair. At worst, however, the reaction mixture (without primers) could be decontaminated by an exonuclease (or a similar enzyme) and the untreated primers could then be added after the exonuclease (or a similar enzyme) had been inactivated. This is less desirable however, since it entails exposure of the reaction mixture to the atmosphere after decontamination and fails to decontaminate the primers themselves.

A non PCR template differs from a PCR product molecule in that the non-PCR product template does not have primer sites near the ends of its DNA chains while the PCR product does. However, unlike the double strand specific exonucleases, certain enzymes (e.g., Bal 31 nuclease), or combinations of enzymes, will degrade both strands of DNA from the ends and will completely digest both types of DNA (i.e., both PCR product DNA and non-PCR product DNA) if given a sufficient period of time. This problem may be avoided by limiting the time of digestion such that only those portions of the DNA chains first digested (i.e., those near the DNA chain ends) are removed by the enzyme. However, this would eliminate one important advantage of exonuclease III (and similar enzymes) in that with Exo III (and similar enzymes) the time of digestion is not critically important and the extent of digestion of the non-contaminant target is therefore easier to control (i.e., it is easier to prevent digestion of non-contaminant target DNA).

EXAMPLE 1

The following reactants were combined to form a reaction mixture. The reaction mixture consisted of 100 mM tris HCl (pH of 8.3), 50 mM KCl, 1.5 mM $MgCl_2$, 100 μg/ml gelatin, 200 μM dATP, 200 μM dCTP, 200 μM dGTP, 200 μM dTTP, 50 picomoles of each primer [essentially the same as were included as control primers in the Amplitaq kit (Cetus)] per 100 μl of solution and 2.5 units of Taq DNA polymerase per 100 μl of solution. The reaction volume was 50 μl.

Fifty picograms of bacteriophage lambda template DNA was added to the reaction volume to form a concentration of 100 picograms per 100 microliters. Exonuclease III was added to obtain a concentration of 80 units per 100 microliters of solution. The mixture was incubated in an automatic temperature cycler (such as is provided by Perkin-Elmer or Ericomp, San Diego, Calif., for example) at 37° for a period of 30 minutes during which any contaminating PCR product DNA is inactivated as template.

Next, the mixture was heated at 94° C. for 7 minutes to inactivate the exonuclease and prevent it from acting on newly amplified DNA. The reaction mixture was then cycled thirty times with each cycle consisting of heating for one minute at 94° C., heating for one minute at 47° C., and heating for three minutes at 72° C. The mixture was then heated at 72° C. for 7 minutes and then kept at 4° C. for at least one hour.

As a result of this procedure, bacteriophage lambda template was amplified and any contaminating PCR product was eliminated as template. It is important to note that all of these heat treatments can be readily programmed into an automatic cycler and therefore require no manipulation of the reaction mixtures. The tubes need not be unsealed after the exonuclease digestion and no opportunity for recontamination from the environment is presented.

II. TREATMENT OF REAGENTS WITH DEOXYRIBONUCLEASE (DNAase) DNAase Digestion

In accordance with the present invention, a GENEAMP™ polymerase chain reaction mixture, that is complete except for target DNA and primer DNA, is treated with DNAase, preferably DNAase 1, at a concentration of 0.1 mg/ml and at a reaction temperature of 37° C. The DNAase is permitted to act upon the reaction mixture for a period of about 30–60 minutes during which all contaminating DNA is digested.

The reaction mixture is then heated to inactivate the DNAase. Preferably, the reaction mixture is heated to about 90° C. for a period of from about 10 to about 30 minutes. Since Taq DNA polymerase is thermostable, it will not be significantly affected by the heat treatment. After the inactivation of the DNAase, the primers and target DNA may be added to the reaction mixture and target DNA replication may proceed. DNAase I is not double strand specific and will digest all DNA including deoxyribonucleotide primers. For this reason, target DNA and primer must be added after the inactivation of DNAase I.

At present it is known that most commercially available preparations of Taq polymerase, are contaminated with DNA from various sources. The present invention can be used to eliminate this contaminant DNA and thereby prevent it from being amplified in a PCR by primers that might be complementary to a target in that DNA.

EXAMPLE 2

The reaction mixture consisted of 7,650 µl of H$_2$O, 100 mM Tris HCl (pH 8.3), 50 mM KCl, 1.5 mM MgCl$_2$, 100 µg/ml gelatin, 200 µl of 10 mM dATP, 200 µl of 10 mM dCTP, 200 µl of 10 mM dTTP, 200 µl of 10 mM dGTP, 50 µl of Taq DNA polymerase (the final concentration of Taq DNA polymerase was 2.5 units per 100 microliter of solution) and 200 µl of 0.1 µg/ml DNAase I, with a total volume of 10,000 µl. The reaction mixture was incubated at 37° C. for 60 minutes. During the incubation, DNAase I acted upon contaminant DNA and digested contaminant DNA such that it could no longer function as a DNA template in a polymerase chain reaction. Next, the reaction mixture was heated at 90° C. for 30 minutes to inactivate the DNAase. After the DNAase has been inactivated, DNA template and primers may be added to the reaction mixture.

As a result of the above process, contaminant DNA was digested such that it could no longer function as a DNA template in a polymerase chain reaction. Consequently, subsequent amplification procedures were successfully carried out using the same reaction mixture.

III. TREATMENT OF REAGENTS WITH RESTRICTION ENDONUCLEASES

An alternative embodiment of the present invention includes the use of Type II restriction endonucleases. The restriction endonucleases cut the contaminant DNA in the interprimer region such that the contaminant DNA may no longer function as a template for PCR amplification. Alternatively, the restriction endonucleases can cut the contaminant PCR product in the region which base pairs with the primer thus preventing efficient priming and therefore preventing amplification of the contaminant PCR product.

Restriction endonucleases are generally double strand specific (i.e., they will cut double stranded DNA but not single stranded DNA). Accordingly, most restriction endonucleases can be added to reaction mixtures which include primers since most restriction endonucleases will not digest single stranded DNA such as PCR primers.

In general, each restriction endonuclease recognizes a specific base sequence or set of related sequences known as a recognition site. The recognition site is usually 4–6 bases in length. In order for the DNA to be cut by the restriction endonuclease, the DNA must have a recognition site specific for the restriction endonuclease. Most restriction enzymes cut both strands of the DNA within the recognition site. Some restriction endonucleases cut the DNA outside of, but close to, the recognition site.

Under certain circumstances, intrastrand base pairing will occur, within single stranded DNA, to form a double stranded region. This can occur, for example, when one of the DNA strands has reversed complementary base sequences (also known as an inverted repeat or dyad symmetry) in linear proximity to one another. Most restriction endonuclease sites have an inverted repeat sequence. Such a complementary base sequence can base pair to itself to form a loop or tee structure (see FIGS. 3a and 3b). The loop or tee may or may not be base paired at the restriction site. The portion of the DNA strand not involved in the loop or tee structure can form a linear DNA sequence that can base pair to a different linear DNA sequence that is complementary to it such that the looped out structure does not interrupt the linear complementary sequence. This is illustrated in FIG. 3A.

Restriction endonucleases can be employed in several ways to prevent amplification of contaminant PCR product DNA. First, the restriction endonuclease can be used to cut a recognition site that happens to be present in the interprimer region of the contaminant PCR product. The target DNA would also be inactivated if it contained a recognition site specific for the restriction endonuclease unless the target DNA were either omitted from the digestion mixture or, alternatively, the target DNA was made single stranded (as for example by heat-denaturation) thereby making it resistant to the (usually) double-strand specific endonuclease.

Alternatively, the restriction endonuclease site could be incorporated into one or both primers and thereby be introduced into the PCR product when it is not present in the original target sequence. This could be done in either of two ways. In a first embodiment, the restriction endonuclease site could be added to the 5' end of the primer where it would not interfere with priming activity for which the 3' end is critical. To allow inactivation of the resulting PCR product, the primer's restriction endonuclease recognition site would have to be recognized by a restriction endonuclease that cuts outside of the recognition site, in a direction 3' to the restriction site. Several such enzymes are presently known, including Fok 1. Such an enzyme, if it cut sufficiently far in the 3' direction, could interrupt the interprimer region and inactivate the PCR product.

Alternatively, if the restriction endonuclease cut closer to the recognition site, the cut would still be within the primer sequence. Nonetheless, the restriction endonuclease would have the effect of reducing the efficiency of priming of the digested contaminant PCR product and thereby inactivate it.

The restriction endonuclease site could also be located within the single stranded primer molecule, at a location other than the 5' end. To preserve the linear base sequence needed to prime the PCR, the restriction site would have to be included in a base sequence which would form a loop or tee structure such that the restriction site protruded from the linear priming sequence and did not prevent priming. Such a linear priming sequence could itself be cut by the restriction endonuclease or the restriction endonuclease could cut 3' to the priming sequence in the interprimer region as described before.

Such a loop or tee-containing primer would itself be resistant to cleavage by double strand specific endonucleases since the site of cutting would be single stranded. For example, if the loop or tee primer were 5 bases long and the restriction endonuclease cut 9 bases away (in a 3' direction) from the recognition site on the primer then, the primer would not be cut by the restriction endonuclease since the restriction endonuclease is specific for double stranded DNA.

In the case of a restriction endonuclease that cut within the recognition site, the primer might be susceptible to cleavage by the restriction endonuclease if there were sufficiently long flanking regions of double strandedness around the recognition site as is required by many, but not all, restriction endonucleases.

After successful priming by such a primer with a loop or tee, the primer would be expected to be copied in a linear form in the second cycle of synthesis so that the molecules amplified thereafter would be primed by primers that did not require looping out of the recognition sequence and thus would be more efficient. However, even if they were not uniformly linearized in this way, the combination of a looped out recognition site in the primer, coupled to a double stranded PCR product would still be expected to form a site for cutting by the restriction endonuclease.

It may be desirable to stabilize a tee or loop structure so as to facilitate the formation of a linear priming sequence. This could be accomplished, for example, by choosing a loop or tee primer with a relatively high guanine-cytosine content or by adding to the recognition sequence additional bases that can base pair in the loop or tee so as to make it more stable. Also, in order to facilitate both intra and intermolecular base pairing of the primer the PCR conditions would have to be individualized for each primer sequence used, at least during the first few cycles. Principally, this would involve lengthening the low temperature, annealing stage of the cycle.

When the present invention is used with the GENE-AMP™ polymerase chain reaction, automation of the amplification process can be provided by using a programmable cycling device and programming the steps of 1) incubating the reaction mixture so as to permit the restriction endonuclease to digest the contaminant DNA, and 2) heating the reaction mixture so as to inactivate the restriction endonuclease.

Another advantage of these digestions (done for the purpose of eliminating contaminant DNA) is that they are carried out in sealed tubes. Suitable cyclers are available from Perkin-Elmer Corp. (761 Main Avenue, Norwalk, Conn. 06859-00122). Since the tubes are sealed for the duration of the amplification process, the risk of introducing contaminants after digestion by the restriction endonuclease is eliminated.

The choice of restriction endonucleases to be used is influenced by several factors. Some of the more important factors, in order of decreasing significance, include heat lability of the restriction endonuclease (i.e., it is preferable that the restriction endonuclease be of the type which is inactivated by the heating of the reaction mixture), the ability of the restriction endonuclease to act under the conditions (pH and salt concentration particularly) of the PCR reaction, the length of the recognition sequence and the base composition of the recognition site.

The larger the length of the recognition sequence the less likely will be the chance occurrence of the recognition sequence within the interprimer region. If the target DNA (or contaminant PCR product) has a recognition sequence in the interprimer region, it will be inactivated by the action of a restriction endonuclease specific for such a recognition site.

The aforementioned methods may be combined where appropriate. For example, exonuclease III and one or more restriction endonucleases may be incorporated into a reaction mixture for more effective digestion of contaminant DNA.

While there have been described what are presently the preferred embodiments of the invention, those skilled in the art will realize that changes and modifications may be made thereto without departing from the spirit of the invention, and it is intended to claim all the changes and modifications as falls within the scope of the present invention.

I claim:

1. A method for the inactivation of contaminant PCR product DNA templates in an amplification reaction mixture, said mixture having at least one contaminant PCR product DNA template, at least one target DNA template, complementary primers to said target DNA template, a heat resistant DNA polymerase and a supply of dNTPs under conditions suitable for maintaining a polymerase chain reaction, which comprises:

a) contacting said mixture With at least one enzyme selected from the group consisting of exonucleases and other enzymes with exonucleolytic properties;

b) incubating said mixture while being contacted with said at least one enzyme at a temperature sufficient and for a time sufficient to permit inactivation of said contaminant PCR product DNA template;

c) incubating the product of step b) at a temperature sufficient and for a time sufficient to permit inactivation of said exonucleases; and d) cycling the product of step c) at temperatures and for times sufficient to permit amplification of the target DNA template.

2. The method of claim 1 wherein the enzyme is T7 exonuclease (gene 6).

3. The method of claim 1 wherein the enzyme is exonuclease III.

4. The method of claim 1 wherein the enzyme is Bal 31 nuclease.

5. The method of claim 1 wherein the heat resistant DNA polymerase is Taq DNA polymerase.

6. The method of claim 1 wherein said exonuclease is T4 DNA polymerase.

* * * * *